(12) United States Patent
Schoenholtz (10) Patent No.: US 6,203,534 B1
(45) Date of Patent: Mar. 20, 2001

(54) CATHETER WITH PROTECTIVE COVERING

(75) Inventor: Jason P. Schoenholtz, Manhattan Beach, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/387,074

(22) Filed: Aug. 31, 1999

Related U.S. Application Data
(60) Provisional application No. 60/148,199, filed on Aug. 10, 1999.

(51) Int. Cl.$^7$ ..................................................... A61M 5/32
(52) U.S. Cl. ............................................................. 604/265
(58) Field of Search ...................... 604/264, 265, 604/51, 523, 524, 528, 531; 138/134, 123–125, 137–139, 74

(56) References Cited

U.S. PATENT DOCUMENTS

| | | | |
|---|---|---|---|
| 3,861,972 | 1/1975 | Glover et al. | 156/86 |
| 4,044,765 | 8/1977 | Kline | 128/214.4 |
| 4,411,055 | 10/1983 | Simpson et al. | 29/447 |
| 5,107,852 | 4/1992 | Davidson et al. | 128/772 |
| 5,499,973 | * 3/1996 | Saab | 604/96 |
| 5,545,151 | * 8/1996 | O'Connor et al. | 604/282 |
| 5,902,268 | * 5/1999 | Saab | 604/96 |
| 5,932,035 | * 8/1999 | Koger et al. | 148/563 |
| 6,016,437 | * 1/2000 | Tu et al. | 600/374 |

* cited by examiner

Primary Examiner—Sharon Kennedy
(74) Attorney, Agent, or Firm—Christie, Parker & Hale, LLP (57) ABSTRACT

A catheter has a shaft with a water-resistant protective covering along its length. The covering protects the catheter shaft, i.e., catheter body and tip section, from the elements of in vivo conditions, i.e., blood and other body fluids, and reduces softening of the catheter over time. The covering also adds a lubricious surface to increase the mobility of the catheter. However, the protective covering does not substantially affect the mechanical properties of the catheter. The covering extends over at least about 50% of the shaft. The covering has a thickness less than about 0.004 inch and is formed of a material having a water vapor transmission rate of less than about 9.0 g-mil/100 in$^2$-24 hr at about 90% relative humidity and about 37° C.

56 Claims, 2 Drawing Sheets

CATHETER WITH PROTECTIVE COVERING

CROSS-REFERENCE TO RELATED APPLICATION

This application claims priority of U.S. Provisional Patent Application No. 60/148,199, filed Aug. 10, 1999, the entire disclosure of which is incorporated herein by reference.

FIELD OF THE INVENTION

The present invention is directed to a catheter shaft with a water-resistant protective covering.

BACKGROUND OF THE INVENTION

Typically, catheters are made of biocompatible plastics such as polyurethane and thermoplastic elastomer resins, such as Pebax®. However, when a catheter made from such a material is used during a surgical procedure, the catheter is kept in the body for periods lasting from one to eight hours. During this time, the plastic of the catheter absorbs body fluids and becomes softer over time. Experiments with typical polyurethane and Pebax shafts soaked in body-temperature distilled water confirm this conclusion. For example, it takes almost twice as much force to bend a dry Pebax® catheter over an angle of 60° compared to a Pebax® catheter soaking for an hour. Further, it takes more than twice as much force to bend a dry polyurethane catheter over an angle of 60° compared to a polyurethane catheter soaking for an hour. As a result, it becomes difficult for a physician to manipulate the catheter over the course of the procedure because the mechanical properties of the catheter change, with the catheter becoming harder to push, pull and turn. For example, a catheter that absorbs moisture looses its "pushability", i.e., tends to perform like a wet noodle, becoming more difficult to push through the body. Additionally, in the case of catheters having a deflectable distal end, as the catheter shaft absorbs moisture, the deflectable distal end responds differently to the same movement of the handle over time. Further, the ability of the distal end to hold the deflection decreases, and it is more difficult to hold against the tissue. Accordingly, a need exists for a catheter that overcomes these disadvantages.

In an attempt to address some of these disadvantages, U.S. Pat. No. 5,545,151 (the '151 patent) discloses a catheter shaft formed from an inner layer of a particular blend of polyester and polyurethane, an outer layer formed from a different blend of polyester and polyurethane, and a reinforcing means therebetween. The '151 patent states that polyester-polyurethane blends are found not to absorb moisture and, hence, will not change in dimension when immersed in saline, body fluids and/or contrast media. However, a catheter shaft formed from a polyester-polyurethane blend has a particular feel and maneuverability that is different, for example, from a catheter shaft formed from polyurethane or Pebax. Physicians develop strong preferences for catheter shafts having a particular feel and mechanical properties, and are often reluctant to use a catheter having a different feel. Accordingly, a need exists for a way to modify a preexisting catheter shaft to reduce its ability to absorb moisture, while at the same time substantially retaining the mechanical properties and feel of the catheter.

SUMMARY OF THE INVENTION

The present invention is directed to a catheter having a shaft with a water-resistant protective covering along its length. The covering protects the catheter shaft, i.e., catheter body and tip section, from the elements of in vivo conditions, i.e., blood and other body fluids, and reduces softening of the catheter over time. The covering also adds a lubricious surface to increase the mobility of the catheter. However, the protective covering does not substantially affect the mechanical properties of the catheter. The protective covering is useful for any catheter or similar medical device, including, but not limited to, electrophysiology catheters and cardiology catheters.

In one embodiment, the invention is directed to a catheter having a shaft comprising a flexible plastic tubing having a least one lumen therethrough. The flexible plastic tubing is provided with a covering over at least about 50% of the shaft. The covering has a thickness less than about 0.004 inch and is formed of a material having a water vapor transmission rate of less than about 9.0 g-mil/100 in$^2$-24 hr as determined by ASTM Test Method E 96 at about 90% relative humidity and about 37° C.

In another embodiment, the invention is directed to a catheter comprising a shaft and a handle. The shaft comprises a catheter body and a catheter tip section. The catheter body comprises a first flexible plastic tubing having proximal and distal ends. The catheter tip section comprises a second flexible plastic tubing mounted at the distal end of the catheter body. The second flexible tubing is more flexible than the first flexible plastic tubing. The shaft further comprises a protective covering over at least 50% of the shaft. The covering is formed of a material having a water vapor transmission rate of less than about 9.0 g-mil/100 in$^2$-24 hr at about 90% relative humidity and about 37° C. The handle is connected to the proximal end of the catheter body. In a particularly preferred aspect of this embodiment, the covering comprises polyester (PET) having a water vapor transmission rate of less than about 2.0 g-mil/100 in$^2$-24 hr at about 90% relative humidity and about 37° C., and the covering has a thickness of less than 0.0005 inch.

The invention is also directed to a catheter comprising a catheter shaft and a protective coating over at least 50% of the catheter shaft. The catheter shaft comprises a flexible plastic tubing made of a first material having a least one lumen therethrough. The protective coating is made of a second material having a lower water vapor transmission rate than the first material.

In another embodiment, the invention is directed to a catheter comprising a shaft and a handle. The shaft comprises a catheter body and tip section. The catheter body, which has at least one lumen extending therethrough, comprises an outer wall formed of a flexible plastic, an inner wall formed of a flexible plastic, and a reinforcement member between the outer wall and the inner wall. The catheter tip section, which is mounted on the distal end of the catheter body and has at least one lumen extending therethrough, comprises an outer wall formed of a flexible plastic, an inner core formed of a flexible plastic, and a reinforcement member between the outer wall and the inner core. The tip section is more flexible than the catheter body. The shaft further comprises a protective covering over at least 50% of its length. The covering is formed of a material having a water vapor transmission rate of less than about 9.0 g-mil/100 in$^2$-24 hr at about 90% relative humidity and about 37° C.

In still another embodiment, the invention is directed to a catheter having a shaft comprising a flexible plastic tubing having a least one lumen therethrough. The flexible plastic tubing is provided with a covering over at least about 90% of the shaft. The covering is formed of a material having a water vapor transmission rate of less than about 9.0 g-mil/100 in$^2$-24 hr at about 90% relative humidity and about 37° C. The percent difference in the bending stiffness of the catheter when provided with the covering compared to the same catheter without a covering is less than about 5% when the catheter is bent at an angle of about 60°.

In yet another embodiment, the invention is directed to a catheter comprising a catheter body and a basket electrode array mounted at the distal end of the catheter body. The catheter body has at least one lumen extending therethrough. The basket electrode array comprises a plurality of flexible arms connected at their proximal and distal ends. Each arm comprises a plastic material carrying at least one electrode. The plastic material of each arm is provided with a protective covering over its length. The protective covering has a water vapor transmission rate of less than about 9.0 g-mil/100 in$^2$-24 hr at about 90% relative humidity and about 37° C.

In yet another embodiment, the invention is directed to a catheter having a shaft comprising a flexible plastic tubing having a least one lumen therethrough. The flexible plastic tubing is provided with a covering over at least about 90% of the catheter shaft. The covering is formed of a material such that the Improvement Value, as defined below, in the bending stiffness of the catheter after being soaked for 1 hour in 37° C. distilled water that is imparted by the covering when the catheter is bent over an angle of 60° is at least about 50%.

The invention is also directed to a method for increasing the water resistance of a catheter having a shaft. The method comprises providing a covering over at least 50% of the shaft with a material having a water vapor transmission rate of less than about 9.0 g-mil/100 in$^2$-24 hr at about 90% relative humidity and about 37° C. A preferred method comprises providing a covering over at least 90% of the shaft with a material that results in less decrease in the bending stiffness of the catheter after being soaked for 1 hour in 37° C. distilled water when the catheter is bent to an angle of 60° compared to a similar shaft without a protective covering. Preferably the difference in bending stiffness is at least 50%. The percentage difference in bending stiffness between a catheter shaft with and without a protective covering after being soaked for 1 hour at 37° C. in distilled water and then bent to an angle of 60° is referred to herein as Improvement Value.

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
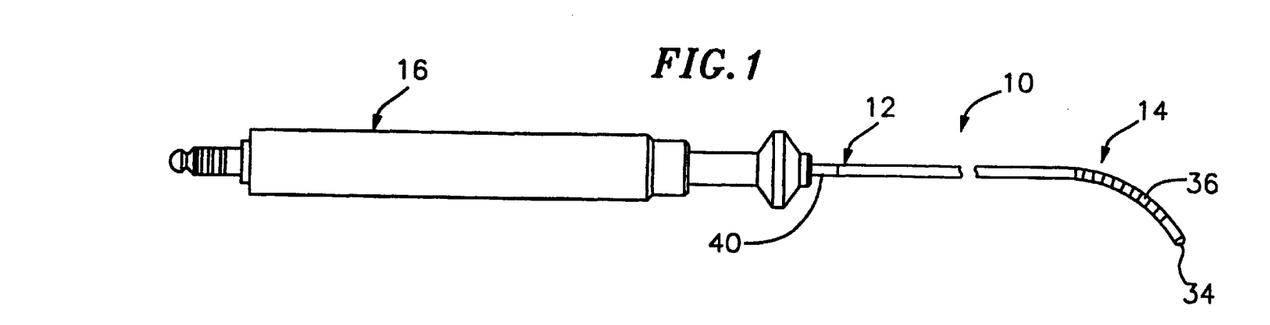
FIG. 1 is a side view of a catheter in accordance with the invention.

In a particularly preferred embodiment of the invention, there is provided a steerable catheter elongated shaft with a protective covering over at least a portion of its outer surface. As shown in FIG. 1, the catheter 10 comprises an elongated catheter body 12 having proximal and distal ends, a tip section 14 at the distal end of the catheter body 12, and a handle 16 at the proximal end of the catheter body 12. The catheter body 12 and tip section 14 make up the shaft of the catheter. If desired, the shaft can comprise only a catheter body.

Figures 2, 3:
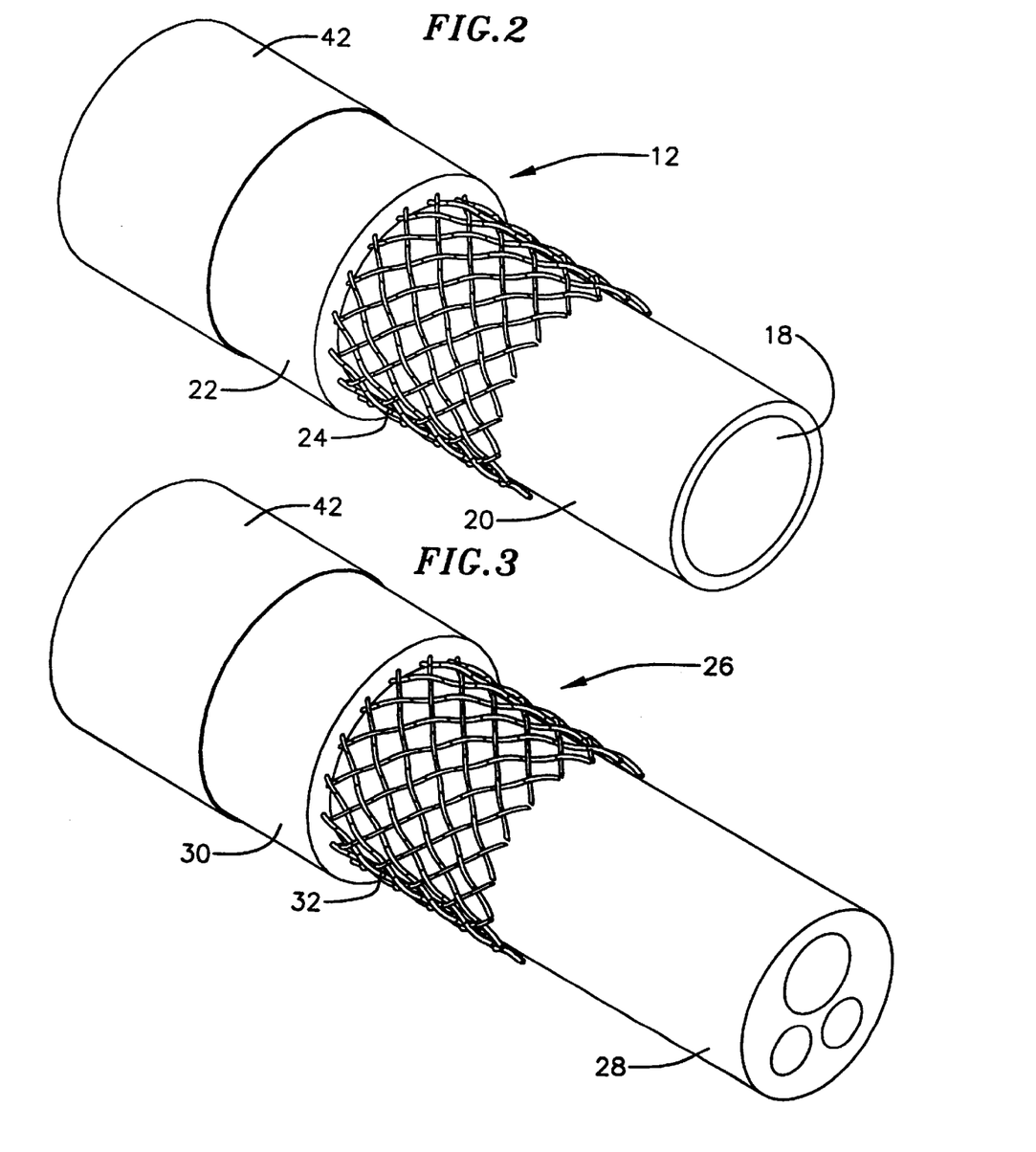
FIG. 2 is a schematic view of the body of a catheter in accordance with the invention.
FIG. 3 is a schematic view of the tip section of a catheter in accordance with the invention.

With reference to FIG. 2, the catheter body 12 comprises an elongated tubular construction having a single central or axial lumen 18, although additional lumens can be provided as desired. The catheter body 12 is flexible, i.e., bendable, but substantially non-compressible along its length. The catheter body 12 can be of any suitable construction and made of any suitable material. A presently preferred construction comprises an inner wall 20 made of a flexible plastic, an outer wall 22 made of a flexible plastic, and a reinforcing member 24 between the inner wall and outer wall. The reinforcing member 24 is preferably a braided mesh of high-strength steel, stainless steel or the like, but could alternatively be a perforated metal tube, a perforated plastic tube, a plastic mesh or a contiguous plastic tube or fabric. This construction increases the torsional stiffness of the catheter body 12 so that, when the handle 16 is rotated, the tip section 14 of the catheter 10 will rotate in a corresponding manner. Examples of flexible plastic materials for the inner wall 20 and outer wall 22 are polyurethane and Pebax. A particularly preferred material for the inner wall 20 and outer wall 12 is a mixture of 60 to 70% pellethane (polyurethane pellets) and the remainder barium sulfate to make the catheter radiopaque. The precise outer diameter of the catheter body 12 is not critical to the present invention, but is preferably no more than about 8 french (0.105 inch), more preferably no more than about 7 french (0.092 inch), and depending on the desired application, no more than about 6 french (0.079 inch) or no more than about 5 french (0.066 inch).

As shown in FIG. 3, the tip section 14 comprises a short section of tubing 26 having three lumens. The tubing 26 is made of a suitable non-toxic and biocompatible material. A presently preferred construction for the tubing 26 is similar to that of the catheter body 12, i.e., an inner core 28 made of polyurethane or PEBAX, an outer wall 30 made of the same material as the inner core, and a reinforcing member 32 between the outer wall and the inner core. However, particularly for a steerable catheter, it is preferred that the tubing 26 is more flexible than the catheter body 12. For example, the catheter body 12 can be formed from a higher durometer plastic than the tip section, or isoplast can be included in the catheter body material to increase its hardness. The number of lumens in the tip section 14 can vary as desired. The outer diameter of the tip section 14, like that of the catheter body 12, is preferably no greater than about 8 french, more preferably no greater than about 7 french, and, depending on the application, no greater than about 5 or 6 french. The sizes of the lumens are not critical to the present invention and depend on the desired application for the catheter.

The proximal end of the catheter body 12 is connected to the handle 16 by means of a shrink sleeve 40 that covers a portion of the outer surface of the catheter body 12. The length of the catheter shaft that extends outside the handle preferably ranges from about 100 cm to about 120 cm, but can vary depending on the desired application.

The handle 16 can be any suitable handle. For example, if the catheter is a deflectable catheter, such as that described in U.S. Pat. Nos. Re 34,502 and 5,897,529, the entire disclosures of which are incorporated herein by reference, a suitable control handle is used, such as that also described in U.S. Pat. Nos. Re 34,502 and 5,897,529. If desired, the catheter can be multi-directional with a suitable control handle, such as described in U.S. Pat. No. 6,123,699 and U.S. Applications Nos. 09/130,359 (filed Aug. 7, 1998), and 09/205,631 (filed Dec. 3, 1998), the entire disclosures of which are incorporated herein by reference.

The outer surface of the shaft is covered with a water-resistant protective covering 42, as shown in FIGS. 2 and 3. The protective covering covers a major part (at least about 50%) of the catheter shaft. Preferably the protective covering covers at least about 80%, more preferably at least about 95%, still more preferably at least about 98%, of the catheter shaft.

The protective covering is made from a material that preferably has a water vapor transmission rate of less than about 9.0 g-mil/100 in$^2$-24 hr, more preferably less than about 4.0 g-mil/100 in$^2$-24 hr, still more preferably less than about 2.0 g-mil/100 in$^2$-24 hr, as determined by ASTM Test Method E 96, incorporated herein by reference, at about 90% relative humidity and about 37° C. If the water vapor transmission rate of the material exceeds about 9.0 g-mil/100 in$^2$-24 hr, the catheter shaft can absorb an amount of bodily fluid that has a significant adverse effect on the mechanical properties of the catheter. One example of a suitable material for the protective covering is polyester (PET) [polyester (polyethylene terephthalate)], such as the Thermoplastic Polyester Shrink Tubing, commercially available from Advanced Polymers, Inc. (Salem, N.H.), which has a water vapor transmission rate of about 1.80 g-mil/100 in$^2$-24 hr at about 90% relative humidity and about 37° C. Another example of a suitable material for the protective covering is parylene (di-para-xylene), such as Parylene N, commercially available from Parylene Coating Services (Katy, Tex.), which has a water vapor transmission rate of about 1.50 g-mil/100 in$^2$-24 hr at about 90% relative humidity and about 37° C. Other mat that can be used for the protective covering include polytetrafluoroethylene and fluorinated ethylene propylene.

The protective covering should be extremely thin so that it does not significantly add diameter to the catheter, which could cause difficulty when the catheter is used with a guiding sheath. More importantly, the covering should be thin so that is does not significantly increase the stiffness or otherwise change the mechanical properties of the pre-coated catheter. Preferably the covering has a thickness of less than about 0.004 inch, more preferably less than about 0.002 inch, still more preferably less than about 0.001 inch, even more preferably less than about 0.0005 inch. A particularly preferred covering is polyester shrink tubing having a thickness of about 0.00025 inch.

The covering can be applied to the catheter shaft by any suitable technique. In a particularly preferred embodiment, the covering is polyester (PET) shrink sleeving. The shrink sleeving is fitted over the shaft by sliding the shaft through the shrink sleeve. The inner diameter of the shrink sleeve should be slightly greater than the diameter of the catheter shaft. For example, for a 7 French catheter shaft, a shrink sleeve having an inner diameter of about 0.100 inch is preferred, and for a 6 French catheter shaft, a shrink sleeve having an inner diameter of about 0.085 inch is preferred. The sleeve is then shrunk by drawing, i.e., pulling the ends to stretch the polyester (PET) shrink sleeve material, while heating it at a temperature of about 85° C. to about 190 ° C., more particularly at a temperature of about 150° C. However, care should be taken when the heat used for the shrinking process, i.e., shrink temperature, exceeds the glass transition temperature of the material of the catheter body and/or tip section, which is about 112° C. for polyurethane. If the shrink temperature exceeds the glass transition temperature of the material for the catheter body and/or tip section, the heat should be applied for a very short time to avoid melting the catheter shaft to an extent that would adversely affect the properties of the catheter, e.g., less than about 5 seconds. However, a higher temperature tends to provide a tighter fit of the shrink sleeve. Moreover, it may be desirable to melt the material of the catheter body and/or tip section slightly so that it bonds to or melts with shrink sleeving used to form the covering. If a catheter is made with the catheter body extruded separately from the tip section, as in the embodiment described above, the shrink sleeve can be formed over the body and tip section independently. Other techniques for applying the covering include extrusion, spraying and dripping.

The covering enhances the ability of the catheter to maintain its mechanical properties after exposure to moisture over an extended period of time. Preferably the covering is selected so that the Improvement Value in the bending stiffness of the catheter shaft catheter soaked for 1 hour in 37° C. distilled water that is imparted by the covering when the catheter is bent over an angle of 60° is at least about 50%, more preferably at least about 60%. The Improvement Value in the bending stiffness is calculated as the difference between the force required to bend the coated soaked catheter and the force required to bend an otherwise identical non-coated soaked catheter, divided by the force required to bend the non-coated catheter. A more detailed explanation of the conditions used to determine the Improvement Value are described in Example 1 below.

It is also important that the covering not significantly affect the mechanical properties of the catheter. Preferably the covering is selected so that the percent difference in the bending stiffness of a dry catheter provided with a covering compared to the same dry catheter without a covering is less than about 5%, more preferably less than about 3%, even more preferably less than about 1%, when the catheter is bent at an angle of about 60°. The percent difference is calculated by taking the absolute value of the difference of the force required to bend the non-coated catheter and the force required to bend the coated catheter, and dividing this value by the force required to bend the non-coated catheter. A more detailed explanation of the conditions used to determine the percent difference in the bending stiffness of the catheter are described in Example 2 below.

Further, the covering preferably does not kink or wrinkle when the catheter is bent. The material of the covering, as well as its thickness, can affect whether it can withstand severe bends in the catheter, e.g., around 180°, without wrinkling or bunching. For example, a thermoplastic polyester shrink sleeve covering having a thickness of about 0.00025 inch does not wrinkle when the catheter is bent at an angle of about 180°.

If desired, the tip section 14 can comprise one or more electrodes mounted thereon. For example, a tip electrode 34 can be mounted on the distal end of the tubing 26, e.g., for mapping or ablation. Examples of suitable tip electrodes and techniques for mounting the tip electrode onto the tubing 26 are disclosed in U.S. Pat. Nos. 6,120,476, filed Dec. 1, 1997, and 5,935,124, filed Dec. 2, 1997, the entire disclosures of which are incorporated herein by reference.

Additionally, one or more ring electrodes 36 can be mounted on the tubing 26, also for mapping or ablation. Examples of suitable ring electrodes and techniques for mounting a ring electrode on the tubing 26 are also disclosed in U.S. Pat. Nos. 6,120,476 and 5,935,124. The ring electrodes are preferably mounted on the tubing 26 after the protective covering has been applied over the tubing.

Figure 4:
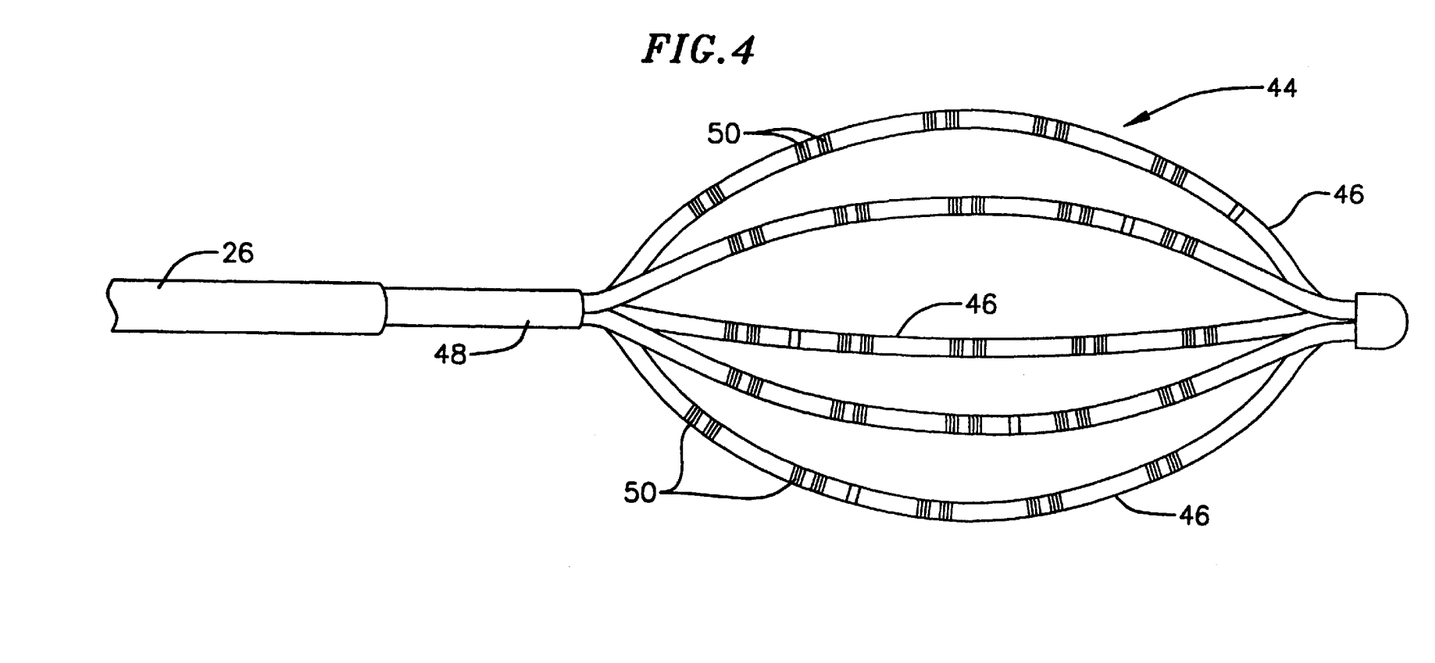
FIG. 4 is a side view of a basket electrode array for a catheter in accordance with the invention.

In another embodiment, the catheter carries a basket electrode array 44 at its distal end, as shown in FIG. 4. The basket electrode array 44 comprises five electrode carrying arms 46 connected to an inner catheter shaft 48 that extends into the distal end of the tubing 26. The inner catheter shaft 48 can be moved relative to the catheter body 12 and tubing 26 of the tip section 14 between an extended position, as shown in FIG. 4, wherein the arms extended completely out the distal end of the catheter 10, and a retracted position wherein the arms 46 are retracted within the tubing 26.

Each arm 46 is formed of a tube of flexible insulating material, e.g., polyurethane. Each arm 46 has its own spaced set of ten electrodes 50, shown in FIG. 4 as bipolar electrode pairs. It is understood that the number of arms 46 and electrodes 50 on each arm may vary as desired. A detailed description of a basket electrode array, including the structure of the arms and the mechanism of use if provided in U.S. Pat. No. 5,628,313, the entire disclosure of which is incorporated herein by reference. In accordance with the present invention, one or more of the arms 46 are provided with a protective covering, as described above, that extends over the length of the flexible insulating material. For each arm, the protective covering preferably covers at least 50%, more preferably at least 90%, more preferably at least 98%, of the length of the arm.

EXAMPLES

Example 1

Samples of catheter shaft having a length of about 6 to 8 inches were tested for bending stiffness. The samples of shaft were taken from a 7 French tubing (outer diameter—0.091 inch; inner diameter 0.063 inch), which is commercially available from Cordis Webster (Diamond Bar, Calif.) under the designation Noga-Star™. The tubing was formed from an inner wall of polyurethane/barium sulfate and an outer wall of polyurethane/barium sulfate/isoplast, with a 0.0026 inch layer of reinforcing stainless steel braid wire therebetween.

Seven of the samples were provided with a polyester (PET) protective covering. The covering was formed by shrinking polyester shrink sleeve (0.00025 inch thickness; 0.100 inch inner diameter) over the shaft at a temperature of about 150° C. for less than 5 seconds. These samples were then soaked for 1 hour in 37° C. distilled water prior to testing. Prior to soaking, the ends of the shaft samples were filled with polyurethane adhesive to cap the ends. Seven of the non-coated samples were also soaked for 1 hour in 37° C. distilled water prior to testing, with their ends also capped with adhesive. Ten non-coated samples were tested without soaking, i.e. dry.

Each short section of shaft was tested on a Tinius Olsen Bending Stiffness Tester with a force fof 0.35 in-lbs. The samples were maintained in a straight position, i.e., were not bent, prior to the test. The percentage of the 0.35 in-lbs force required to bend the sample the designated number of degrees was recorded, and is provided below in Tables 1 to 3.

Table 1 further provides the Improvement Value in the bending stiffness of the catheter shaft. The Improvement Value in the bending stiffness was calculated as the difference between the force required to bend the coated soaked catheter and the force required to bend the non-coated soaked catheter, divided by the force required to bend the non-coated catheter. This data shows that the covering enhances the ability of the catheter to maintain its mechanical properties.

TABLE 1-7

French Catheter
Polyester Covering - 1 Hour Soak

| Sample | 10 deg | 20 deg | 30 deg | 40 deg | 50 deg | 60 deg | 70 deg | 80 deg | 90 deg |
|---|---|---|---|---|---|---|---|---|---|
| 1 | 13.00 | 23.50 | 30.50 | 35.00 | 37.50 | 40.00 | 41.00 | 41.50 | 42.50 |
| 2 | 14.00 | 24.00 | 30.50 | 34.50 | 37.00 | 40.00 | 41.00 | 41.00 | 41.50 |
| 3 | 12.50 | 21.00 | 28.00 | 32.00 | 35.00 | 37.50 | 39.00 | 40.00 | 40.00 |
| 4 | 12.50 | 21.00 | 28.00 | 31.00 | 34.00 | 35.50 | 36.50 | 36.50 | 37.00 |
| 5 | 13.00 | 23.00 | 30.50 | 35.00 | 39.00 | 40.00 | 41.50 | 42.00 | 42.50 |
| 6 | 13.00 | 22.00 | 29.50 | 33.50 | 37.50 | 39.50 | 40.00 | 40.00 | 40.50 |
| 7 | 12.50 | 22.00 | 29.50 | 32.50 | 36.00 | 37.50 | 39.00 | 40.00 | 40.50 |
| Average | 12.93 | 22.36 | 29.50 | 33.36 | 36.57 | 38.57 | 39.71 | 40.14 | 40.64 |
| SD | 0.53 | 1.18 | 1.12 | 1.57 | 1.69 | 1.77 | 1.73 | 1.80 | 1.89 |
| Improvement Value | 81% | 82% | 82% | 70% | 68% | 64% | 63% | 62% | 62% |

TABLE 2-7

French Catheter
No Covering - 1 Hour Soak

| Sample | 10 deg | 20 deg | 30 deg | 40 deg | 50 deg | 60 deg | 70 deg | 80 deg | 90 deg |
|---|---|---|---|---|---|---|---|---|---|
| 1 | 8.50 | 14.00 | 18.50 | 22.00 | 24.00 | 25.00 | 26.50 | 27.50 | 28.00 |
| 2 | 6.50 | 11.00 | 15.00 | 18.00 | 19.50 | 21.00 | 22.00 | 22.50 | 22.50 |
| 3 | 7.00 | 12.50 | 16.00 | 20.00 | 22.00 | 23.50 | 25.00 | 25.00 | 25.00 |

TABLE 2-7-continued

French Catheter
No Covering - 1 Hour Soak

| Sample | 10 deg | 20 deg | 30 deg | 40 deg | 50 deg | 60 deg | 70 deg | 80 deg | 90 deg |
|---|---|---|---|---|---|---|---|---|---|
| 4 | 7.00 | 13.00 | 16.50 | 19.50 | 22.00 | 23.50 | 24.50 | 25.00 | 25.50 |
| 5 | 7.50 | 12.00 | 16.50 | 20.00 | 22.50 | 24.00 | 25.00 | 25.50 | 26.50 |
| 6 | 7.50 | 12.50 | 16.50 | 20.00 | 22.50 | 24.00 | 25.00 | 25.50 | 25.50 |
| 7 | 6.00 | 11.00 | 14.50 | 17.50 | 20.00 | 24.00 | 22.00 | 22.50 | 22.50 |
| Average | 7.14 | 12.29 | 16.21 | 19.57 | 21.79 | 23.57 | 24.29 | 24.79 | 25.07 |
| SD | 0.80 | 1.07 | 1.29 | 1.48 | 1.55 | 1.24 | 1.68 | 1.78 | 2.01 |

Table 3 provides the ratio of the weight required to bend the non-coated catheter after soaking to the weight required to bend the dry uncoated catheter (NC Soak:NC Dry), which is generally around 0.50: 1. Table 3 further provides the ratio of the weight required to bend the coated catheter after soaking to the weight required to bend the dry uncoated catheter (C Soak:NC Dry), which is generally around 0.85:1. This data shows that the protective covering substantially maintained the catheter's mechanical properties after soaking.

TABLE 3-7

French Catheter
No Covering - No Soak

| Sample | 15 degrees | 30 degrees | 45 degrees | 60 degrees | 75 degrees | 90 degrees |
|---|---|---|---|---|---|---|
| 1 | 22.00 | 35.50 | 42.00 | 46.00 | 46.00 | 46.00 |
| 2 | 22.00 | 35.50 | 42.00 | 46.00 | 46.00 | 46.00 |
| 3 | 21.00 | 34.00 | 42.00 | 46.00 | 47.00 | 47.00 |
| 4 | 21.50 | 33.50 | 41.50 | 45.50 | 47.00 | 47.00 |
| 5 | 22.00 | 35.00 | 43.50 | 48.50 | 51.00 | 51.00 |
| 6 | 21.50 | 35.00 | 42.00 | 45.50 | 46.50 | 46.50 |
| 7 | 22.00 | 35.00 | 43.00 | 46.00 | 47.50 | 48.00 |
| 8 | 22.00 | 35.00 | 42.00 | 45.50 | 46.00 | 46.00 |
| 9 | 22.50 | 35.00 | 42.50 | 46.00 | 47.00 | 47.00 |
| 10 | 21.00 | 34.00 | 41.00 | 45.00 | 46.00 | 46.00 |
| Average | 21.72 | 34.67 | 42.17 | 46.00 | 47.11 | 47.17 |
| SD | 0.51 | 0.66 | 0.75 | 1.00 | 1.56 | 1.58 |
| NC Soak: NC Dry | — | 0.47:1 | — | 0.51:1 | — | 0.53:1 |
| C Soak: NC Dry | — | 0.85:1 | — | 0.84:1 | — | 0.86:1 |

Example 2

Samples of catheter shaft having a length of about 6 to 8 inches were tested for bending stiffness. The samples of shaft were taken from a 6 French tubing (outer diameter—0.078 inch; inner diameter 0.047 inch) that is commercially available from Cordis Webster (Diamond Bar, Calif.) under the designation D-1086. The tubing is formed from an inner wall of polyurethane/barium sulfate/isoplast and an outer wall of polyurethane/barium sulfate/isoplast, with a 0.0026 inch layer of reinforcing stainless steel braid wire therebetween.

Four of the samples were provided with a polyester (PET) protective covering. The covering was formed by shrinking polyester tubing (0.00025 inch thickness; 0.085 inch inner diameter) over the shaft at a temperature of about 150° C. for less than 5 seconds. Another four samples were provided without the covering.

Each sample was tested on a Tinius Olsen Bending Stiffness Tester with a force of 0.25 in-lbs. The samples were maintained in a straight position, i.e., were not bent, prior to the test. The percentage of the 0.25 in-lbs force required to bend the sample the designated number of degrees was recorded, and is provided below in Tables 4 and 5.

TABLE 4-6

French Catheter
Covering - Dry

| Sample | 15 degrees | 30 degrees | 45 degrees | 60 degrees | 75 degrees | 90 degrees |
|---|---|---|---|---|---|---|
| 1 | 19.00 | 29.50 | 36.00 | 40.50 | N/A | 44.00 |
| 2 | 20.00 | 30.00 | 37.00 | 41.00 | 43.00 | 44.00 |
| 3 | 21.00 | 31.00 | 37.00 | 40.50 | 42.00 | 42.50 |
| 4 | 20.00 | 31.00 | 37.50 | 41.50 | 43.50 | 43.50 |
| Average | 20.33 | 30.67 | 37.17 | 41.00 | 42.83 | 43.33 |
| SD | 0.58 | 0.58 | 0.29 | 0.50 | 0.76 | 0.76 |

Table 5 provides the percent difference in the bending stiffness of the catheter when provided with a covering. The percent difference is calculated by taking the absolute value of the difference of the force required to bend the non-coated catheter and the force required to bend the coated catheter, and dividing this value by the force required to bend the non-coated catheter. This data indicates that the covering did not significantly affect the mechanical properties of the dry catheter.

TABLE 5-6

French Catheter
No Covering - Dry

| Sample | 15 degrees | 30 degrees | 45 degrees | 60 degrees | 75 degrees | 90 degrees |
|---|---|---|---|---|---|---|
| 1 | 20.00 | 31.00 | 37.00 | 39.50 | 41.50 | 42.00 |
| 2 | 21.00 | 32.00 | 38.00 | 41.00 | 43.00 | 44.00 |
| 3 | 20.00 | 31.00 | 36.50 | 39.00 | 41.00 | 41.00 |
| 4 | 20.00 | 32.00 | 39.00 | 42.00 | 42.50 | 42.00 |
| Average | 20.33 | 31.67 | 37.83 | 40.67 | 42.17 | 42.33 |
| SD | 0.58 | 0.58 | 1.26 | 1.53 | 1.04 | 1.53 |
| % Difference | 0 | 3.2% | 1.7% | 0.8% | 1.6% | 2.4% |

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter having a shaft comprising a flexible plastic tubing having an outer surface and at least one lumen therethrough, wherein the flexible plastic tubing is provided with a covering over at least about 50% of the catheter shaft, wherein the covering has an inner surface and the entire inner surface is in direct contact with the outer surface of the flexible plastic tubing, and further wherein the covering has a thickness less than about 0.004 inch and is formed of a material having a water vapor transmission rate of less than about 9.0 g-mil/100 in$^2$-24 hr at about 90% relative humidity and about 37° C.

2. A catheter according to claim 1, wherein the covering has a water vapor transmission rate of less than about 4.0 g-mil/100 in$^2$-24 hr at about 90% relative humidity and about 37° C.

3. A catheter according to claim 1, wherein the covering has a water vapor transmission rate of less than about 2.0 g-mil/100 in$^2$-24 hr at about 90% relative humidity and about 37° C.

4. A catheter according to claim 1, wherein the covering has a thickness of less than about 0.002 inch.

5. A catheter according to claim 1, wherein the covering has a thickness of less than about 0.001 inch.

6. A catheter according to claim 1, wherein the covering has a thickness of less than about 0.0005 inch.

7. A catheter according to claim 1, wherein the covering covers at least about 80% of the shaft.

8. A catheter according to claim 1, wherein the covering covers at least about 95% of the shaft.

9. A catheter according to claim 1, wherein the covering covers at least about 98% of the shaft.

10. A catheter according to claim 1, wherein the covering is a shrink sleeve.

11. A catheter according to claim 1, wherein the covering comprises polyester (PET).

12. A catheter according to claim 1, wherein the covering comprises polyester (PET) having a water vapor transmission rate of less than about 2.0 g-mil/100 in$^2$-24 hr at about 90% relative humidity and about 37° C., and wherein the covering has a thickness of less than 0.0005 inch.

13. A catheter according to claim 1, wherein the Improvement Value in the bending stiffness of the catheter after being soaked for 1 hour in 37° C. distilled water that is imparted by the covering when the catheter is bent over an angle of 60° is at least about 50%.

14. A catheter according to claim 1, wherein the Improvement Value in the bending stiffness of the catheter after being soaked for 1 hour in 37° C. distilled water that is imparted by the covering when the catheter is bent over an angle of 60° is at least about 60%.

15. A catheter according to claim 1, wherein the percent difference in the bending stiffness of the catheter when provided with the covering compared to the same catheter without a covering is less than about 5% when the catheter is bent at an angle of about 60°.

16. A catheter according to claim 1, wherein the percent difference in the bending stiffness of the catheter when provided with the covering compared to the same catheter without a covering is less than about 3% when the catheter is bent at an angle of about 60°.

17. A catheter according to claim 1, wherein the percent difference in the bending stiffness of the catheter when provided with the covering compared to the same catheter without a covering is less than about 1% when the catheter is bent at an angle of about 60°.

18. A catheter comprising:
a shaft comprising:
    a catheter body comprising a first flexible plastic tubing having an outer surface, proximal and distal ends, and at least one lumen extending therethrough;
    a catheter tip section comprising a second flexible plastic tubing mounted at the distal end of the catheter body having an outer surface and at least one lumen extending therethrough, wherein the second flexible tubing is more flexible than the first flexible plastic tubing; and
    a protective covering over at least 50% of the shaft, wherein the covering has an inner surface and the entire inner surface is in direct contact with the outer surface of the first flexible plastic tubing and/or the outer surface of the second flexible plastic tubing, and further wherein the covering is formed of a material having a water vapor transmission rate of less than about 9.0 g-mil/100 in$^2$-24 hr at about 90% relative humidity and about 37° C.; and
a handle connected to the proximal end of the catheter body.

19. A catheter according to claim 18, wherein the covering has a water vapor transmission rate of less than about 4.0 g-mil/100 in$^2$-24 hr at about 90% relative humidity and about 37° C.

20. A catheter according to claim 18, wherein the covering has a water vapor transmission rate of less than about 2.0 g-mil/100 in$^2$-24 hr at about 90% relative humidity and about 37° C.

21. A catheter according to claim 18, wherein the covering has a thickness of less than about 0.004 inch.

22. A catheter according to claim 18, wherein the covering has a thickness of less than about 0.002 inch.

23. A catheter according to claim 18, wherein the covering has a thickness of less than about 0.001 inch.

24. A catheter according to claim 18, wherein the covering has a thickness of less than about 0.0005 inch.

25. A catheter according to claim 18, wherein the covering covers at least about 80% of the shaft.

26. A catheter according to claim 18, wherein the covering covers at least about 95% of the shaft.

27. A catheter according to claim 18, wherein the covering covers at least about 98% of the shaft.

28. A catheter according to claim 18, wherein the covering is a shrink sleeve.

29. A catheter according to claim 18, wherein the covering comprises polyester (PET).

30. A catheter according to claim 18, wherein the covering comprises polyester (PET) having a water vapor transmission rate of less than about 2.0 g-mil/100 in$^2$-24 hr at about 90% relative humidity and about 37° C., and wherein the covering has a thickness of less than 0.0005 inch.

31. A catheter according to claim 30, wherein the covering covers at least 95% of the shaft.

32. A catheter according to claim 18, wherein the Improvement Value in the bending stiffness of the catheter after being soaked for 1 hour in 37° C. distilled water that is imparted by the covering when the catheter is bent over an angle of 60° is at least about 50%.

33. A catheter according to claim 18, wherein the Improvement Value in the bending stiffness of the catheter after being soaked for 1 hour in 37° C. distilled water that is imparted by the covering when the catheter is bent over an angle of 60° is at least about 60%.

34. A catheter according to claim 18, wherein the percent difference in the bending stiffness of the catheter when provided with the covering compared to the same catheter without a covering is less than about 5% when the catheter is bent at an angle of about 60°.

35. A catheter according to claim 18, wherein the percent difference in the bending stiffness of the catheter when provided with the covering compared to the same catheter without a covering is less than about 3% when the catheter is bent at an angle of about 60°.

36. A catheter according to claim 18, wherein the percent difference in the bending stiffness of the catheter when provided with the covering compared to the same catheter without a covering is less than about 1% when the catheter is bent at an angle of about 60°.

37. A catheter according to claim 18, wherein the first flexible plastic tubing comprises polyurethane or Pebax.

38. A catheter according to claim 37, wherein the covering comprises polyester (PET) having a water vapor transmission rate of less than about 2.0 g-mil100 in$^2$-24 hr at about 90% relative humidity and about 37° C., and wherein the covering has a thickness of less than 0.0005 inch.

39. A catheter comprising:
a shaft comprising:
a catheter body having proximal and distal ends and at least one lumen extending therethrough, the catheter body comprising:
an outer wall formed of a flexible plastic;
an inner wall formed of a flexible plastic; and
a reinforcement member between the outer wall and the inner wall;
a catheter tip section mounted on the distal end of the catheter body and having at least one lumen extending therethrough, the tip section comprising:
an outer wall formed of a flexible plastic;
an inner core formed of a flexible plastic; and
a reinforcement member between the outer wall and the inner core;
wherein the tip section is more flexible than the catheter body; and
a protective covering over at least 50% of the shaft, wherein the covering is formed of a material having a water vapor transmission rate of less than about 9.0 g-mil/100 in$^2$-24 hr at about 90% relative humidity and about 37° C.; and
a handle connected to the proximal end of the catheter body.

40. A catheter having a shaft comprising a flexible plastic tubing having an outer surface and at least one lumen therethrough, wherein the flexible plastic tubing is provided with a covering over at least about 90% of the catheter shaft, wherein the covering has an inner surface and the entire inner surface is in direct contact with the outer surface of the flexible plastic tubing, and further wherein the covering is formed of a material having a water vapor transmission rate of less than about 9.0 g-mil/100 in$^2$-24 hr at about 90% relative humidity and about 37° C., and further wherein the percent difference in the bending stiffness of the catheter when provided with the covering compared to the same catheter without a covering is less than about 5% when the catheter is bent at an angle of about 60°.

41. A catheter according to claim 40, wherein the percent difference in the bending stiffness of the catheter when provided with the covering compared to the same catheter without a covering is less than about 3% when the catheter is bent at an angle of about 60°.

42. A catheter according to claim 40, wherein the percent difference in the bending stiffness of the catheter when provided with the covering compared to the same catheter without a covering is less than about 1% when the catheter is bent at an angle of about 60°.

43. A catheter comprising:
a catheter body having proximal and distal ends and at least one lumen extending therethrough;
a basket electrode array mounted at the distal end of the catheter body, the basket electrode array comprising a plurality of flexible arms having distal and proximal ends, said arms being connected at their proximal and distal ends, each arm comprising a plastic material carrying at least one electrode, wherein the plastic material of each arm is provided with a protective covering over its length, the protective covering having a water vapor transmission rate of less than about 9.0 g-mil/100 in$^2$-24 hr at about 90% relative humidity and about 37° C.

44. A catheter having a shaft comprising a flexible plastic tubing having an outer surface and at least one lumen therethrough, wherein the flexible plastic tubing is provided with a covering over at least about 90% of the catheter shaft, wherein the covering has an inner surface and the entire inner surface is in direct contact with the outer surface of the flexible plastic tubing, and further wherein the covering is formed of a material such that the Improvement Value in the bending stiffness of the catheter after being soaked for 1 hour in 37° C. distilled water that is imparted by the covering when the catheter is bent over an angle of 60° is at least about 50%.

45. A catheter according to claim 44, wherein the Improvement Value in the bending stiffness of the catheter after being soaked for 1 hour in 37° C. distilled water that is imparted by the covering when the catheter is bent over an angle of 60° is at least about 60%.

46. A catheter according to claim 44, wherein the covering has a thickness of less than about 0.004 inch.

47. A catheter according to claim 44, wherein the covering has a thickness of less than about 0.002 inch.

48. A catheter according to claim 44, wherein the covering has a thickness of less than about 0.001 inch.

49. A catheter according to claim 44, wherein the covering has a thickness of less than about 0.0005 inch.

50. A catheter comprising:
a catheter shaft comprising a flexible plastic tubing made of a first material having an outer surface and at least one lumen therethrough; and
a protective covering made of a second material over at least 50% of the catheter shaft, wherein the covering has an inner surface and the entire inner surface is in direct contact with the outer surface of the flexible plastic tubing, and further wherein the second material has a lower water vapor transmission rate than the first material.

51. A catheter according to claim 50, wherein the covering has a thickness of less than about 0.004 inch.

52. A catheter according to claim 50, wherein the percent difference in the bending stiffness of the catheter when provided with the covering compared to the same catheter without a covering is less than about 5% when the catheter is bent at an angle of about 60°.

53. A method for increasing the water resistance of a catheter having a shaft, comprising providing a covering over at least 50% of the shaft with a material having a water vapor transmission rate of less than about 9.0 g-mil/100 in$^2$-24 hr at about 90% relative humidity and about 37° C.

54. A method for increasing the water resistance of a catheter having a shaft, comprising providing a covering over at least 90% of the shaft with a material that results in an Improvement Value in the bending stiffness of the catheter after being soaked for 1 hour in 37° C. distilled water that is imparted by the covering when the catheter is bent over an angle of 60° of at least about 50%.

55. A catheter according to claim 39, wherein the covering has an inner surface and the entire inner surface is in direct contact with the outer wall of the catheter body and/or the outer wall of the tip section.

56. A method according to claim 53, wherein the shaft has an outer wall, and wherein the covering has an inner surface, whereby the entire inner surface is in direct contact with the outer wall.

* * * * *